US006206850B1

(12) United States Patent
O'Neil

(10) Patent No.: US 6,206,850 B1
(45) Date of Patent: Mar. 27, 2001

(54) PATIENT CONTROLLABLE DRUG DELIVERY SYSTEM FLOW REGULATING MEANS

(75) Inventor: Alexander George Brian O'Neil, 102 Lawler Street, Subiaco (AU), 6008

(73) Assignees: Christine O'Neil; Alexander George Brian O'Neil, both of Subiaco (AU)

(*) Notice: Subject to any disclaimer, the term of this patent is extended or adjusted under 35 U.S.C. 154(b) by 0 days.

(21) Appl. No.: 09/142,678

(22) PCT Filed: Mar. 14, 1997

(86) PCT No.: PCT/AU97/00167

§ 371 Date: Nov. 16, 1998

§ 102(e) Date: Nov. 16, 1998

(87) PCT Pub. No.: WO97/33637

PCT Pub. Date: Sep. 18, 1997

(30) Foreign Application Priority Data

Mar. 14, 1996 (AU) .................................................. PN8701
Mar. 14, 1996 (AU) .................................................. PN8702

(51) Int. Cl.[7] .................................................. A61M 5/14
(52) U.S. Cl. ........................... 604/80; 604/132; 604/247; 604/407
(58) Field of Search ................................ 604/80, 81, 82, 604/83, 132, 133, 257, 246, 247, 407–409

(56) References Cited

U.S. PATENT DOCUMENTS 3,056,403  10/1962  Geweeke .
3,153,414  10/1964  Beall et al. .
4,474,574  10/1984  Wolfe et al. .
5,356,375  * 10/1994  Higley .................................... 604/247
5,505,707  *  4/1996  Manzie et al. ........................ 604/247
5,911,708  *  6/1999  Teirstein ................................ 604/247
6,059,747  *  5/2000  Bruggeman et al. ................. 604/247

FOREIGN PATENT DOCUMENTS 0 067 458     12/1982   (EP) .
0 172 586      2/1986   (EP) .
2 588 757      4/1987   (FR) .
WO 86/03978    7/1986   (WO) .
WO 87/00758    2/1987   (WO) .
WO 91/08002    6/1991   (WO) .
WO 93/00944    1/1993   (WO) .
WO 93/10831    6/1993   (WO) .

* cited by examiner

Primary Examiner—Richard K. Seidel
Assistant Examiner—Jeremy T Thissell
(74) Attorney, Agent, or Firm—Merchant & Gould P.C.

(57) ABSTRACT

A patient controllable drug delivery system including a metering device (30) having an intermittent dose reservoir (34) and a plunger, a main reservoir (26), a fill line (32 connecting the main reservoir (26) and the intermittent reservoir (34) via a metering device fill point (26) and a flow regulating means (10) between the metering device (30) and the patient line (36), the flow regulating means (10) comprising a means for receiving and dispensing a dose of drug (12) and a pressure set one way valve (16), the intermittent dose reservoir (34) and the patient line (36) being in restricted fluid communication, dispensation of the drug being effected by pressure applied by the receiving and dispensing means (12). Systems for the supply of a continuous dose in addition to the patient controllable delivered dose, and a secondary delivery system are also disclosed.

19 Claims, 7 Drawing Sheets

PATIENT CONTROLLABLE DRUG DELIVERY SYSTEM FLOW REGULATING MEANS

The present invention relates to a flow regulating means that forms a portion of the patient controllable drug delivery system. The present invention also relates to a patient controllable drug delivery system and in particular relates to a system which allows for continuous infusion of a drug, while also allowing for separately controlled (by patient, physician or nursing staff) intermittent surges of the same drug. The system is particularly useful in the administration of analgesics.

BACKGROUND OF THE INVENTION

It has been recognised for some time that patient controlled drug administration is desirable in many situations of chronic or temporary (such as post operative) pain. Before the advent of patient controlled analgesia, analgesia relied on periodic injections of drugs by a physician or nurse, typically at four hour intervals. This has the disadvantage that for long periods the patient's analgesic level is significantly above or below the optimum level.

Patient controlled analgesia improves on that prior art by enabling the infusion of small quantities of analgesics at regular intervals as perceived to be required by the patient. That prior art has also further developed to include apparatus and devices which allow for the continuous infusion of analgesics, with or without the need for patient control.

One form of such a device is described in the applicant's published international patent application WO 93/00944. In that publication, there is described an apparatus for patient controlled infusion of a drug, the apparatus allowing for intermittent administration of an analgesic or the like, the intermittency of the administration being controlled by the use of a small bore tube in the controlled refilling of a metering device, such that the patient may not administer further doses too rapidly after previous doses.

However, this system does not provide for the apparatus to be also used to continuously infuse analgesics or the like. The apparatus also would not prevent a patient from administering a dose earlier than recommended, albeit a dose of smaller volume than a full dose.

Another problem with prior art patient controllable drug delivery systems relates to the actuation of the metering device that delivers the drug. In general, metering devices in prior art systems must be actuated for prolonged periods to deliver the drug to the patient via relatively narrow conduits or tubing. In this respect, the prior art metering devices must be actuated for a sufficient time to deliver the drug to the patient against the pressure produced by the narrow conduits or tubing. The prolonged actuating periods of the prior art metering devices prevents their use by certain patients who are weakened or otherwise unable to actuate the metering device for a sufficient length of time Furthermore, when the prior art systems are controlled by nursing staff or the like they are required to remain with the patient for as long as it takes to actuate the metering device.

The system of the present invention aims to provide for separately controlled intermittent surges of a drug, such as an analgesic. Preferred forms of the present invention aim to provide for the continuous infusion of the drug as well as for separately controlled intermittent surges of the same drug. The system also aims to provide for the control of the intermittent surges so as to ensure the necessary time delay between surges, particularly where the system is patient controlled, as opposed to being controlled by a physician or by nursing staff. Finally, the present invention also aims to provide a separately controllable (by patient, physician or nursing staff) system with a relatively short actuation time.

SUMMARY OF THE INVENTION

Thus, the present invention provides a patient controllable drug delivery system capable of delivering a drug to a patient via a patient line, the system including: (i) a main reservoir for holding the drug; (ii) a metering device comprising an intermittent dose reservoir and a plunger biased towards a retracted position; (iii) a fill-line located between the main reservoir and the intermittent dose reservoir which allows continuous fluid communication between the main reservoir and the intermittent dose reservoir via a metering device fill-point; and (iv) a flow regulating means located in-line between the metering device and the patient line, wherein the flow regulating means comprises:

(a) a pressure set one-way valve; and (b) a means for receiving and dispensing a dose of drug, said means having an inlet means and an outlet means through which a drug may pass;

characterised in that the one-way valve is located prior to the inlet, the valve is closed when the flow regulating means is dispensing a drug and open when receiving a drug.

Preferably, the flow regulating means comprises a deformable reservoir. The remainder of the description in respect of the flow regulating means itself will be limited to this preferred form.

The deformable reservoir may be a length of elastomeric tubing or an elastomeric balloon member. In this configuration, the dispensation of the drug via the outlet is achieved by the pressure applied by the deformable reservoir and is at least partially dependent on the amount of deformation of the reservoir and the rate at which the reservoir returns to its pre-deformed state.

The flow regulating means may further comprise a housing which preferably acts as a limiting means for restricting the deformation of the deformable reservoir. Preferably. the housing at least partially surrounds the deformable reservoir. In one particular form, the housing is transparent and is capable of being dismantled to allow the deformable reservoir to be serviced or replaced as required.

Alternatively, the flow regulating means may comprise a cylinder, such as a syringe, having a piston therein for moving the drug in the cylinder to an outlet at one end of the cylinder; the piston and cylinder being relatively movable under the action of a spring which may be disposed internally or externally of the cylinder. In this configuration, the dispensation of the drug is preferably achieved by a syringe with a sprung plunger which exerts a predetermined pressure on the drug.

The pressure set one way valve may be any type of suitable valve that will only open when a predetermined pressure has been met. Preferably, the valve is provided proximal to the inlet of the deformable reservoir. In one particular form, the valve is provided integrally with the inlet of the deformable reservoir. It will be appreciated that the valve controls the passage of the drug to the deformable reservoir and is preferably adapted to allow a surge of drug to the deformable reservoir.

As indicated above the flow regulating means of the present invention is adapted for use in patient controllable drug delivery system. Whilst this specification makes repeated reference to "patient controllable" it will be appreciated that the drug delivery systems of the present invention may be operated by persons other than the patient such as medical staff or the like.

After actuation of the metering device by a patient, physician or nursing staff, so as to empty the intermittent dose reservoir and cause a surge of drug to the patient, the biasing of the plunger towards its retracted position causes a vacuum to be formed therewithin, the vacuum assisting in drawing drug via the fill-line from the main reservoir. By predetermining the strength of the bias on the plunger of the metering device, together with the amount of force being applied to the main reservoir to force drug therefrom, and more importantly by predetermining the diameter of the bore of the fill-line (which may itself be an inline flow resistor of the type mentioned above), the speed with which the intermittent dose reservoir is refilled may be controlled. With this in mind, and due to the pressure-set one way valve only being openable once the intermittent dose reservoir is completely refilled, the speed with which the metering device refills will determine the frequency with which the patient may infuse of intermittent surges of drug. Indeed, the patient's requirements, together with the nature of the drug being administered, will together determine the allowable frequency of surges of drug, which will in turn dictate the preferred speed with which the metering device refills.

The pressure-set one way valve may be any type of suitable valve that will only open when a predetermined pressure has been met. It will be appreciated that the particular pressure required to open the valve will be entirely dependent upon the patient's requirements, the nature of the drug being administered, and the configuration of the particular metering device being utilized. By taking all of these factors into account, the amount of drug to be administered may be determined, the preferred frequency of administration may be determined, the preferred speed of filling the metering device may be determined, and the pressure exertable by the plunger in the metering device may be determined. Once that pressure has been determined, a pressure-set one way valve having particular pressure requirements may then be selected.

The metering device may be varied provided it is capable of drawing a dose of drug from the main reservoir and delivering the dose to the patient via the flow regulating means.

Thus, the metering device may be a syringe type device having a biased plunger. Alternatively, the metering device may comprise an intermittent dose reservoir operably connected to a pump means, the pump means being capable of drawing drug from the main reservoir and delivering the dose to the patient via the flow regulating means.

These configurations allows the operator (patient) to actuate the metering device and administer a predetermined dose of drug as required and incorporates a lock out feature that prevents the operator from administering the drug in an undesirable fashion. In this respect, the inclusion of the flow regulating means with the pressure-set one way valve, having an opening pressure requirement that will only be achievable once a full dose has entered the reservoir of the metering device, ensures that the operator (patient) is unable to infuse an additional dose within an unacceptably short time-frame after having previously infused a complete dose therefrom.

Furthermore, when the metering device contains a full dose and is actuated by the operator (patient) a single actuation delivers the full dose to the patient via the flow regulating means. The patient is not required to actuate the metering device for a prolonged period to deliver the full dose.

The drug delivery system of the present invention may also be configured to administer a continuous dose of drug as well as the operator (patient) controllable dose. The administration of the continuous dose provides a base level of drug dosed to the patient and is in addition to the patient controllable dose that may be administered by the patient as required.

The continuous dose may be delivered in a variety of ways. For example, the main reservoir may further comprise a means for continuously discharging the drug at a predetermined rate through the patient line via an in-line flow resistor.

Thus, the present invention also provides a patient controllable drug delivery system capable of delivering a drug to a patient via a patient line, the system including (i) a metering device having an intermittent dose reservoir and a plunger biased towards a retracted position; (ii) a main reservoir for holding the drug and being capable of continuously discharging the drug at a predetermined rate through the patient line via an in-line flow resistor; (iii) a fill-line located between the main reservoir and the intermittent dose reservoir which allows continuous fluid communication between the main reservoir and the intermittent dose reservoir via a metering device fill-point; and (iv) a flow regulating means located in-line between the metering device and the patient line; wherein the intermittent dose reservoir and the patient line are in restricted fluid communication, the restriction being provided by the flow regulating means.

The continuous delivery of the drug may also be achieved by a secondary drug delivery system that is adapted to deliver a continuous dose to the patient via an in-line flow resistor. In this respect, the secondary drug delivery system may also serve as a back-up delivery system should the primary delivery system fail.

Thus, the present invention also provides a patient controllable drug delivery system capable of delivering a continuous dose of a drug and an intermittent patient controllable dose of a drug, the system comprising a secondary drug delivery system.

The secondary drug delivery system may include a pressure driven secondary main reservoir that delivers the drug to the patient line via an in-line flow resistor.

The in-line flow resistor may be varied provided it is capable of controlling the flow of fluid passing through it. Thus, the in-line flow resistor may comprise flow control tubing which allows a fluid to pass through it at a predetermined rate. Alternatively, the in-line flow resistor may comprise a conduit, such as tubing, provided integrally with a resistor such as a valve or the like.

Thus, the secondary drug delivery system may comprise a secondary flow regulating means capable of receiving and dispensing a dose of drug to the patient line via an in-line flow resistor in the form of flow control tubing.

The systems employing a secondary drug delivery system can act as a back-up in the event that the primary drug delivery system fails. One possible reason for the failure of the primary system could be the jamming of the valve of the flow regulating means in the closed position. This configuration allows a continuous supply of drug to be provided (by the main reservoir) at a low rate over a long period of time, with extra doses being infused by the patient (for example) as required.

The in-line flow resistor is preferably a small bore plastic tube having a relatively thick wall, the latter ensuring that the tube does not kink in use. The small bore of the tube provides significant flow resistance in relation to given liquids and thus determines the flow rate of the liquid therethrough. Such a tube and the method of producing it are described in the applicant's published international patent application WO 88/02637.

It will be appreciated that in this preferred form, the lumen diameter of the small bore tube will be selected in accordance with the patient's requirements and the type of drug being administered in order to ensure an appropriate flow-rate of drug. In this respect, the system of the present invention provides a direct line of flow from the constantly pressurised main reservoir through the small bore tube to the patient. The type of small bore tube utilized will thus dictate the rate of delivery of the drug from the main reservoir.

The main reservoir may be of any suitable form. When the main reservoir is responsible for the continuous supply of the drug as well as supplying the drug to the metering device, it and may conveniently be in the form of a cylinder, such as a syringe, having a piston therein for moving the fluid in the cylinder to an outlet at one end of the cylinder; the piston and cylinder being relatively movable under the action of a spring which may be disposed internally or externally of the cylinder. Alternatively, the main reservoir may be in the form of an expandable resilient bladder member which can be inflated with fluid to pressurise it, the pressure then being relieved by outflow of the fluid through the flexible tube, which may be in the form of flow control tubing. Alternatively, and when the main reservoir is not responsible for the continuous supply of the drug, it may be provided by a tube or the like. In this form, the drug in the tube is transferred to the metering device via the fill-line under suction produced by the biased plunger of the metering device.

The main reservoir is preferably capable of holding large volumes of drug, such as 30 mL or more, to minimise the need for refilling and also to ensure suitable capacity to both provide the continual flow of drug (when required) and also the continual refilling of the smaller volume, intermittent dose reservoir of the metering device.

The metering device is also preferably a syringe, such as an aspirating syringe, whose plunger is biased towards a retracted position by (for example) a return spring. The volume of the intermittent dose reservoir defined by the syringe is preferably relatively small, such as up to 2 to 5 mL. The volume is preferably alterable so as to provide a range of possible volumes, such as by being able to fix the retracted position of the plunger at different points along the metering device.

Where appropriate, the components of the system of the present invention may be adapted to be re-filled as required. For instance, the main reservoir may include a fill means that enables it to be re-filled as required. Preferably, the fill means incorporates a filter or the like to enable the main reservoir to be re-filled without contamination occurring. Similarly, when the main reservoir is provided as a tube incorporating a fill means in the form of a port, the tube may also incorporate a filter at its uppermost end to prevent contamination when the tube is being refilled.

The present invention will now be described in relation to the accompanying drawings. However, it is to be appreciated that the following description is not to limit the generality of the above description.

Figure 1:
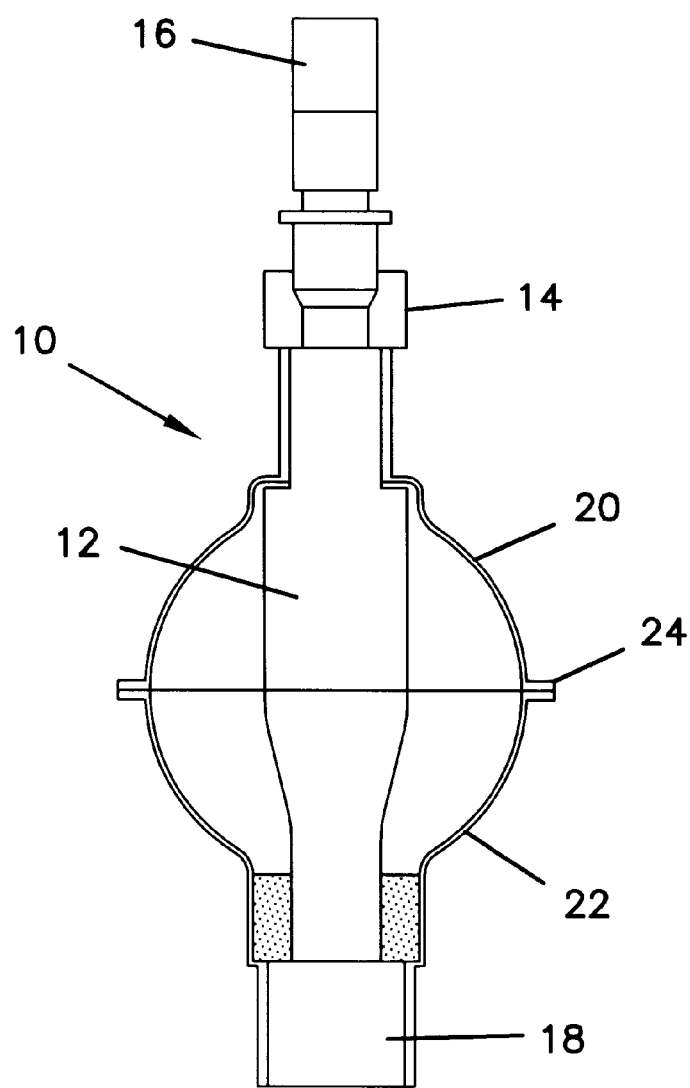
FIG. 1 is a flow regulating means according to a preferred embodiment of the present invention.

The flow regulating means of FIG. 1, generally indicated by the numeral 10, has a receiving and dispensing means in the form of a deformable reservoir 12 with an inlet 14 for receiving a predetermined dose of drug from a metering device (not shown) via a pressure set one way valve 16 and an outlet 18 through which the drug is dispensed, the inlet 14 and outlet 18 are located at respective ends of the deformable reservoir 12. The deformable reservoir 12 is surrounded by a transparent housing having two parts 20, 22 releasably joined at flange 24.

Figure 2:
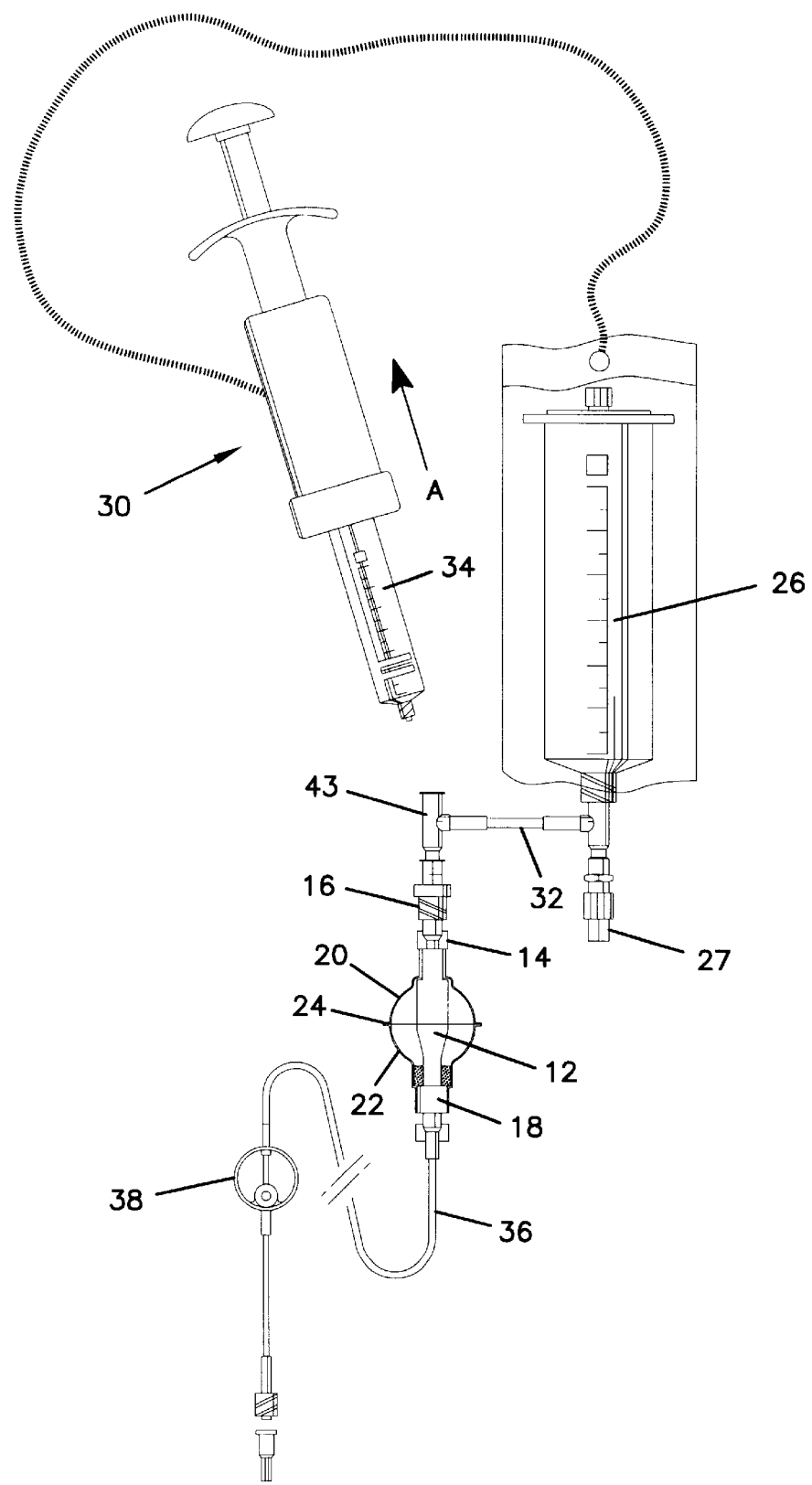
FIG. 2 is a schematic representation of a patient controllable drug delivery device according to a first preferred embodiment of the present invention for administering drugs to a patient.

FIG. 2 illustrates a patient controllable drug delivery system that may be operated by a patient or medical personnel to deliver intermittent doses of a drug. The numerals used to designate parts in FIG. 1 have been retained where appropriate.

A main reservoir in the form of a tube 26 serves as a drug source to which drugs in fluid form may be added as required via injection port 27, the injection port preferably incorporates a filter to prevent contamination during re-filling of the tube 26. The tube 26 is connected to a metering device 30 via a fill-line 32, the metering device 30 also having an intermittent dose reservoir 34 and a plunger (not shown) biased towards a retracted position (in the direction of arrow A) via a spring (not shown). The metering device 30 receives a predetermined amount of drug from the tube 26 at a predetermined rate.

Operation of the metering device 30 delivers a dose of fluid to the deformable reservoir 12 via the pressure set one way valve 16. On receipt of the fluid the deformable reservoir 12 expands, and on contraction dispenses the fluid through outlet 18 to patient-line 36. The fluid passes through the patient-line 36 to the patient via air filter 38 which removes air bubbles from the fluid prior to delivery to the patient.

In use the device of FIG. 2 allows for the delivery of relatively large doses of drugs to a patient through the single operation of the metering device 30. The inclusion of the flow regulating means allows for a dose of drug to be delivered to a patient at a predetermined rate and avoids the need to repeatedly operate a delivery button or pump to deliver the drug over a predetermined period of time. This is especially important for patients who are not physically able to repeatedly operate a pump or delivery button, as it enables them to operate the pump once and receive drugs over an extended- period of time. Further, when the device is being operated by medical staff, drug administration is less labour intensive which offers obvious advantages.

Figure 3:
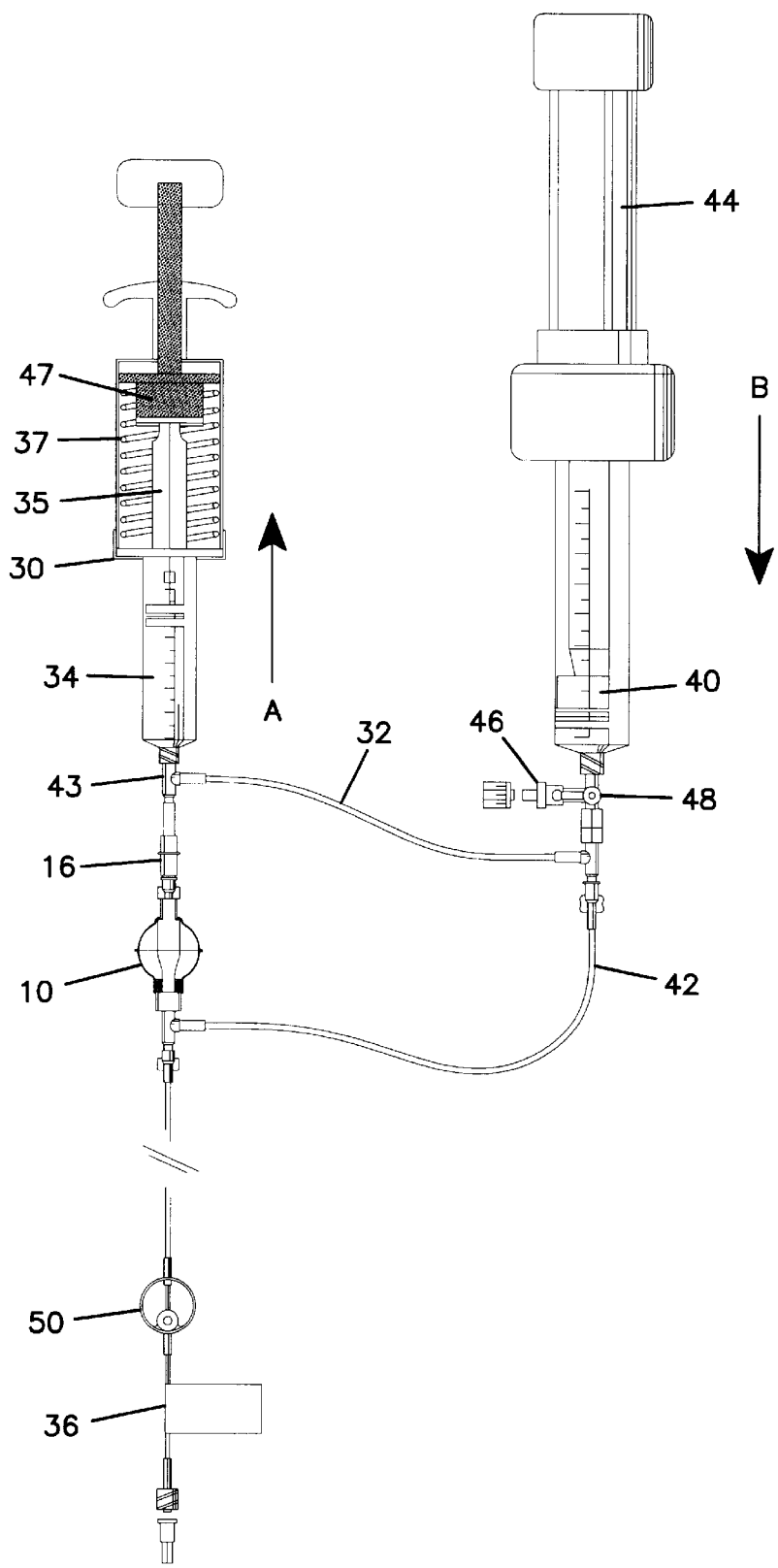
FIG. 3 is a schematic representation of a patient controllable drug delivery system in accordance with a second preferred embodiment of the present invention.

Illustrated in FIG. 3 is a patient controllable drug delivery system which is adapted to administer a continuous dose of drug in addition to the intermittent dose of drug administered by a patient, the system comprising a metering device 30 having an intermittent dose reservoir 34 and a plunger 35 biased towards a retracted position (in the direction of arrow A) via a spring 37. The system also includes a main reservoir 40 which is under constant pressure (in the direction of arrow B) so as to be capable of continuously discharging a drug through a patient line 36, via an in-line flow resistor 42.

Located between the main reservoir 40 and the flow resistor 42 is a fill-line 32, preferably formed of flow control tubing, which allows continuous fluid communication between the intermittent dose reservoir 34 and the main reservoir 40 via a metering device fill-point 43.

The intermittent dose reservoir 34 and the patient line 36 are also in fluid communication, but are in restricted fluid communication. The restriction in the fluid communication therebetween is provided by a flow regulating means comprising (i) a pressure-set one way valve 16 located after the fill-point 43 and, (ii) a receiving and dispensing means in the form of a deformable reservoir 12 between the one way valve and a point before the flow resistor 42.

The valve 16 is adapted such that the pressure required to open the valve 16 (and thus administer a surge of drug to the patient from the intermittent dose reservoir 34) is only achievable by the metering device 30 once the intermittent dose reservoir 34 has been completely filled with drug from the main reservoir 40 via the fill-line 32.

Thus, in operation, after priming the system with drug such that all lines are filled with drug and both reservoirs 34 and 40 are filled with drug, the continuous pressure applied by the pressure mechanism 30 is sufficient to ensure continuous passage of drug through the flow resistor 42 and then through the patient line 36 to be administered to a patient via a catheter attached thereto (not shown). As mentioned above, the in-line flow resistor 42 is preferably a small bore tube whose lumen diameter has been selected in accordance with the required flow rate of a drug being administered to a particular patient.

During operation of the system in this manner, the pressure mechanism 30 will also be applying pressure upon fluid in the fill-line 32 and then in turn on the fluid in the intermittent dose reservoir 34 and the fluid within the upstream side of the one way valve 16. However, this pressure will not be so great as to, by itself, breach the pressure-set one way valve and thus cause additional drug to flow therethrough, and will also not cause movement of the plunger 35 so as to increase the volume of the intermittent dose reservoir 34. On this last point, movement of the plunger 35 is restricted by a spacer 47 whose size and configuration is selected in accordance with the volume required for the intermittent dose reservoir 34.

Thus, during normal operation, there is a continuous flow of drug from the main reservoir 40, via the in-line flow resistor 42 and the patient line 36, to the patient.

By determining the pressure requirement of the pressure-set one way valve 16 to be such that upon actuation of the plunger 35 in the direction opposite to the direction of arrow A, the pressure applied to the full dose in the reservoir 34 is large enough to reach the predetermined breaching pressure of the one way valve 16, when the plunger 35 is depressed, the patient (or a physician or nursing staff) is able to cause a surge of drug of a volume determined by the volume of the intermittent dose reservoir 34, to the patient via the patient line 36.

It will be noted that the combined pressure applied by the pressure mechanism 44 to the main reservoir 40, together with the flow restriction caused by the fill-line 32, prevents any drug from passing through the fill-line 32 from fill-point 26 to the main reservoir 40, when such a surge of drug is delivered.

In a preferred form, the pressure mechanism 44 is a device manufactured and sold by Go Medical Industries Pty Ltd referred to as a "springfuser". This mechanism is described in the applicant's Australian patent number 606092.

Additional to the features described above, the patient controllable drug delivery system of the present invention may also include a branch 46 secured in-line via a three way valve 48, the additional branch 46 providing a point at which air may be removed from the system, that air having been introduced either inadvertently or at the initial priming of the system, the branch 46 also being useable to refill that main reservoir 40. The three way valve 48 may also be configured such that it may be actuated to close off the main reservoir 40. This may be required when operating the metering device 30 to deliver a surge of drug.

Additionally, the patient line 36 may include therewithin a filter 50 of known type for preventing passage of bacteria, including a hydrophilic membrane which discharges to atmosphere any air which inadvertently enters the system.

The tube utilized as the small bore tube of the in-line flow resistor 42, and also (in some forms of the invention) as the fill-line 32, may have a very narrow bore and a relatively thick wall. The tube may be of any suitable length as determined by the required configuration of the system and may for instance be of a length in the order of 5 cm to 20 cm. The lumen diameter of the tube may be in the range of 0.025 mm to 0.20 mm, of course depending upon the particular requirements.

It should also be noted that the use of such fine bore tubing not only sets the rate of continuous delivery of drug (and the refill time of the reservoir 34) but also acts as a safety factor in inhibiting syphoning of liquid from the reservoir 34 to the patient.

Figure 4:
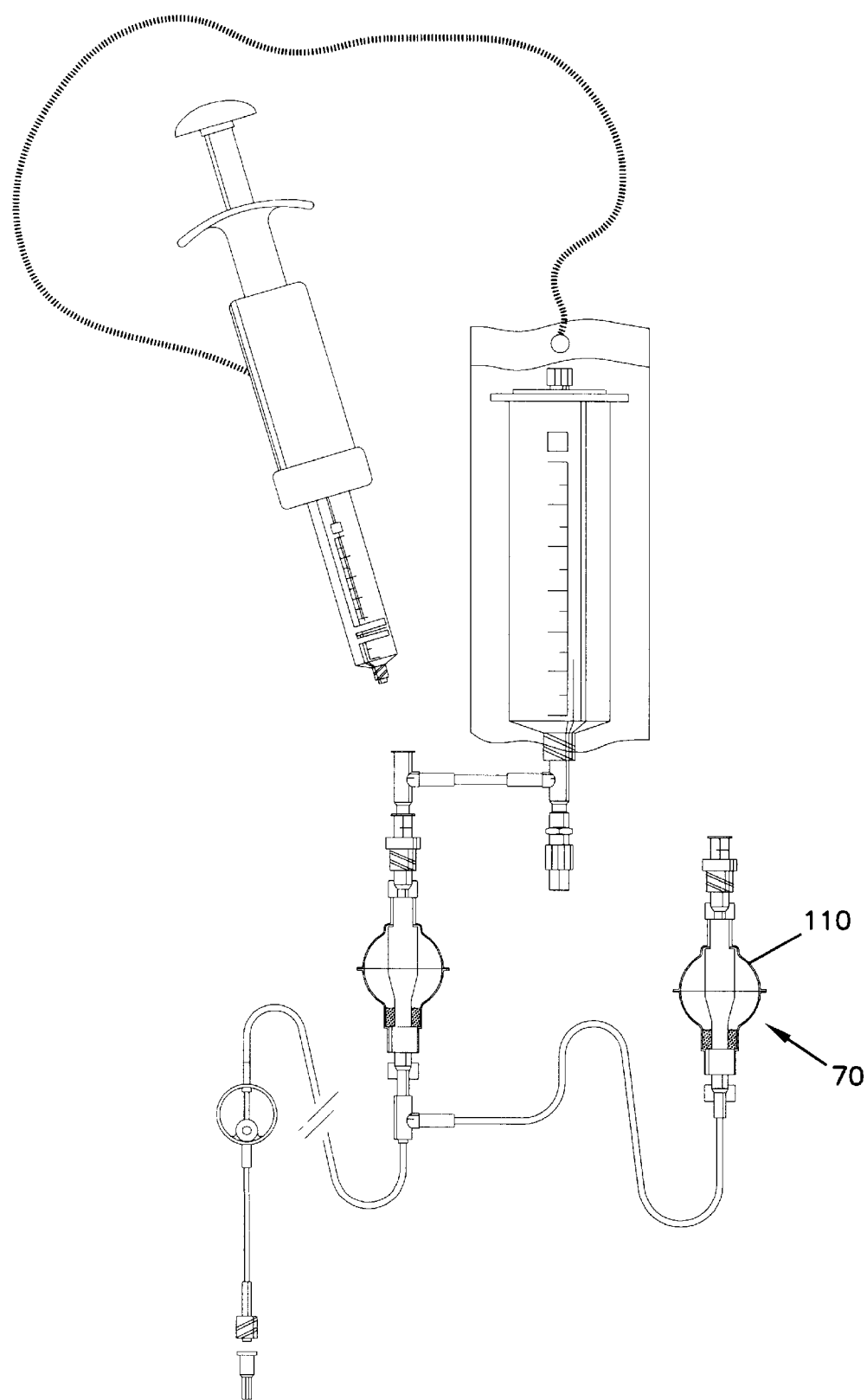
FIG. 4 is a schematic representation of a patient controllable drug delivery system in accordance with a third preferred embodiment of the present invention.

FIG. 4 illustrates a patient controllable drug delivery system which is also adapted to deliver continuous doses of drug as well as the intermittent patient delivered doses, the system incorporating a back-up or secondary drug delivery system. The system is identical to that shown in FIG. 2 save for the secondary drug delivery system, generally indicated by the numeral 70. The secondary drug delivery system in the embodiment includes a secondary flow regulating means 110. The secondary drug delivery system 70 may be utilized to deliver a continuous dose of drug as required or a dose of drug to a patient when the flow regulating means 10 fails, for whatever reason.

As previously indicated, the secondary drug delivery system may also be provided by a syringe, having a piston therein for moving the drug in the cylinder to an outlet at one end of the cylinder; the piston and cylinder being relatively movable under the action of a spring which may be disposed internally or externally of the cylinder and the outlet being in fluid communication with the patient line via an in-line flow resistor.

Figure 5:
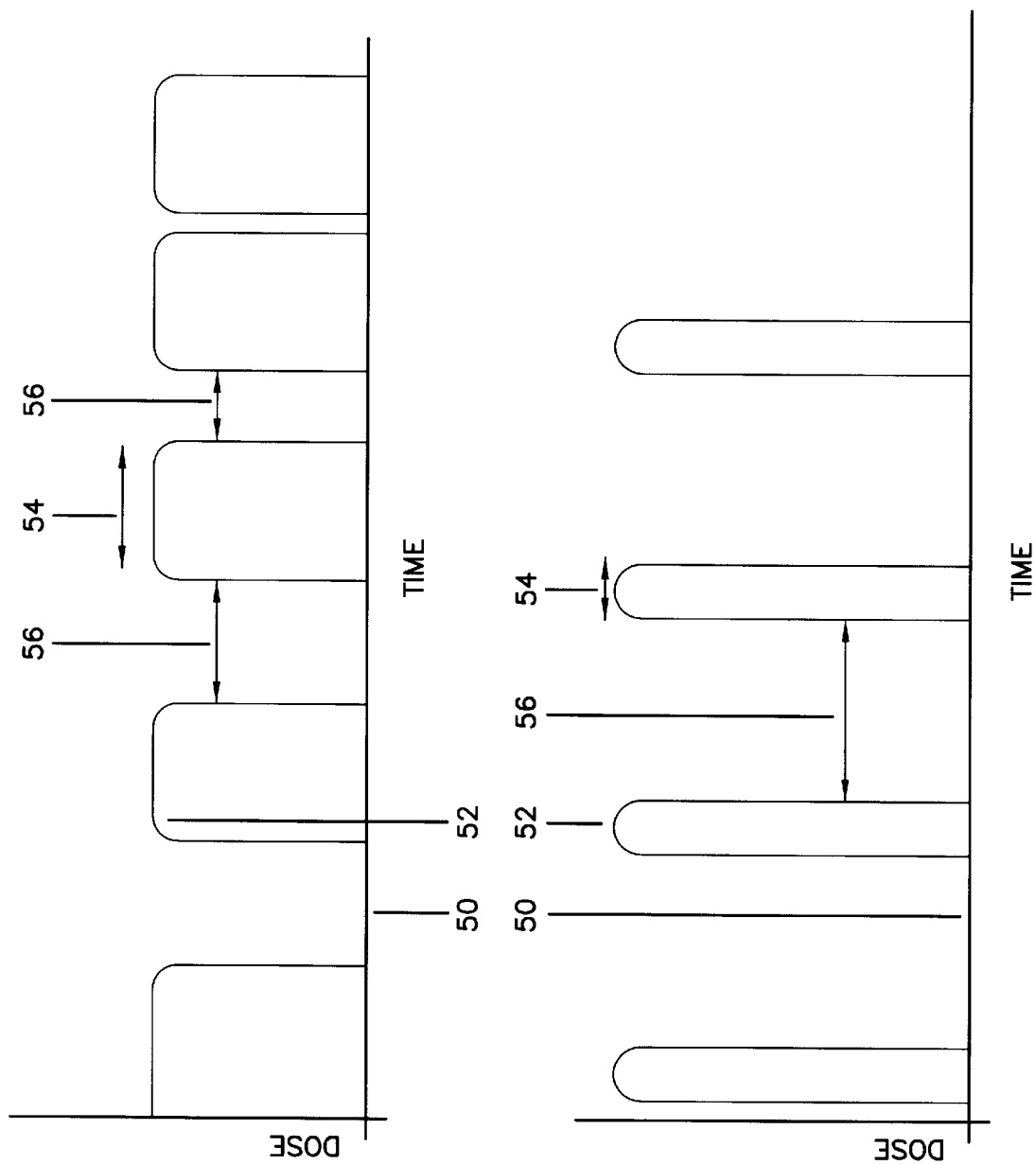
FIG. 5 is a plot of dose Vs time illustrating the dose profile achievable using the drug delivery devices of FIGS. 2 to 4.

FIGS. 5a and 5b show a comparison of drug dose profiles that may be achieved with the drug delivery system of the present invention. The profiles have a base dose 50 and an elevated dose 52 delivered over time 54.

The elevated dose 52 is set to a predetermined amount as required. The elevated dose in FIG. 5a is less than that in FIG. 5b and is delivered over a longer period of time when compared to that of FIG. 5b. These characteristics of the profiles may be modified by varying the particular flow regulating means used.

The profiles also illustrate the lock out time 56 which represents the time between operations of the pump by the patient or medical personnel. The lock out time may be varied as required and is dependent on the rate at which the intermittent reservoir of the metering device fills. The lockout time in FIG. 5a is slightly more than that in FIG. 5b and shows the variable nature of this time period as may be expected during operation by a patient who is receiving drugs to alleviate pain episodes.

When the drug delivery system delivers a continuous dose as well as the patient controllable dose the base dose 50 may be varied as desired and is at least partially dependent on the in-line flow resistor. When there is no continuous delivery the based dose will be nil and the only dose delivered will be the patient controllable dose.

Figure 6:
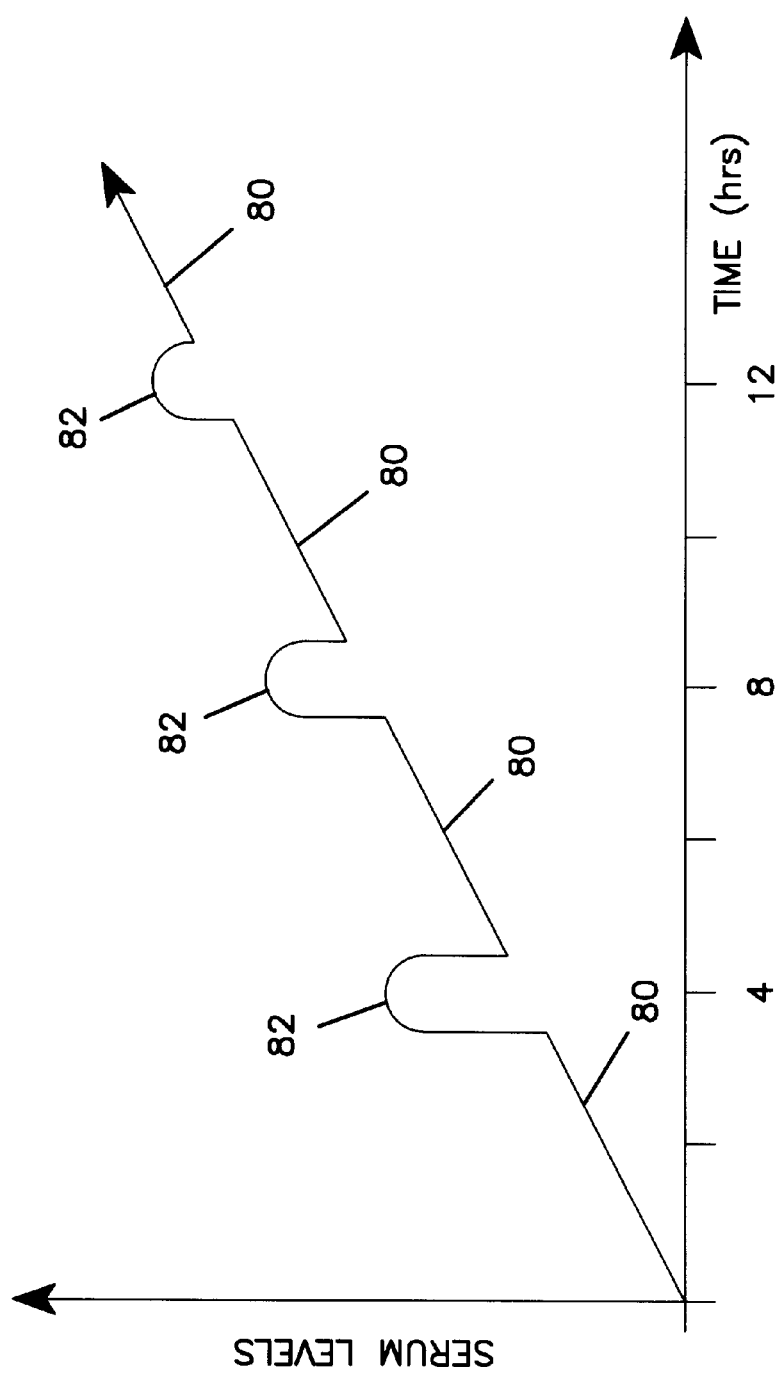
FIG. 6 is a schematic graphical representation of the serum levels of drug achievable by the use of the embodiments of FIG. 3 or 4.

FIG. 6 is a schematic graphical representation showing an example of an opiate delivery technique for pain treatment administering analgesics using the system of the present invention. The graph shows the serum levels obtained with constant and patient controllable drug infusion. The continuous drug delivery results in a steady increase in serum drug levels 80 and is interspersed with spikes 82 which represent the intermittent, patient initiated surges of drug from the metering device.

Figure 7:
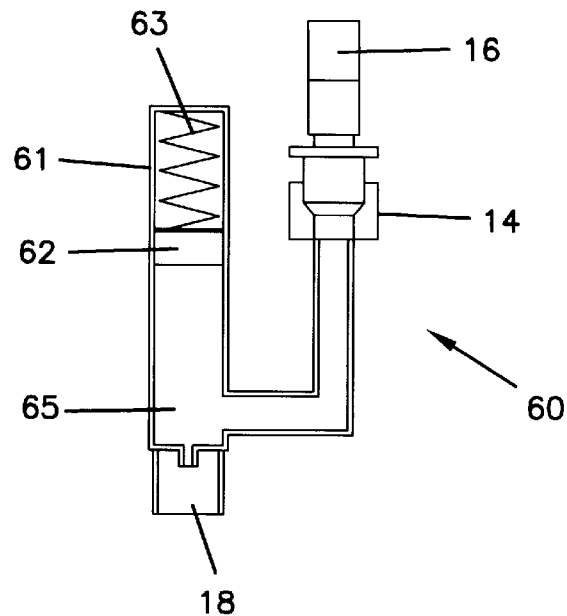
FIG. 7 is a flow regulating means according to a further embodiment which includes an internally disposed spring.

An alternative embodiment of the flow regulating means is shown in FIG. 7. In this embodiment, the flow regulating means 60 comprises a receiving and dispensing means in the form of a cylinder 61 having a piston 62 therein. The cylinder 61 and piston 62 define a receiving chamber 65 of variable volume into which a predetermined dose of drug enters under pressure through the inlet 14. The piston 62 is movable within the cylinder 61 to vary the volume of the receiving chamber. Entry of the drug into the receiving chamber 65 causes the piston to move against the influence of a spring 63 to expand the volume of the receiving chamber 65 and so accommodates the incoming drug. The spring 63 is accommodated internally within the cylinder 61 on the opposed side of the piston 62 to the receiving chamber 65. Once all of the predetermined dose of drug has entered the receiving chamber 65, the piston 62 is caused to undergo return movement under the influence of the spring, thereby exerting pressure on the drug in the receiving chamber 65, causing the drug to be dispensed through outlet 18.

Figure 8:
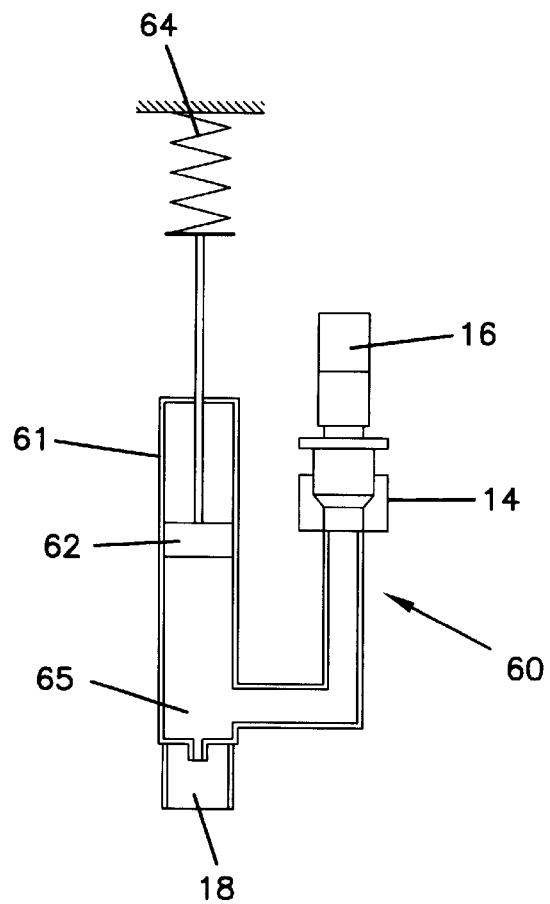
FIG. 8 is a flow regulating means according to a still further embodiment which includes an externally disposed spring.

A further embodiment of the flow regulating means is shown in FIG. 8. This further embodiment is similar to the embodiment shown in FIG. 7 except that the spring 64 in FIG. 8 is disposed externally of the cylinder 61.

Finally, it will be appreciated that there may be other variations and modifications to the configurations described herein that are also within the scope of the present invention.

The claims of the invention are as follows:

1. A patient controllable drug delivery system capable of delivering a drug to a patient via a patient line, the system including: (i) a main reservoir for holding the drug; (ii) a metering device comprising an intermittent dose reservoir and a plunger biased towards a retracted position; (iii) a fill-line located between the main reservoir and the intermittent dose reservoir which allows continuous fluid communication between the main reservoir and the intermittent dose reservoir via a metering device fill-point; and (iv) a flow regulating means located in-line between the metering device and the patient line, wherein the flow regulating means comprises:

(a) a pressure set one-way valve; and
(b) a means for receiving and dispensing a dose of drug, said means having an inlet means and an outlet means through which a drug may pass;

characterised in that the one-way valve is located prior to the inlet, the valve is closed when the flow regulating means is dispensing a drug and open when receiving a drug.

2. A drug delivery system according to claim 1 wherein the flow regulating means comprises a cylinder, having a piston therein for moving the drug in the cylinder to an outlet at one end of the cylinder; the piston and cylinder being relatively movable under the action of a spring which may be disposed internally or externally of the cylinder.

3. A drug delivery system according to claim 1 wherein the flow regulating means comprises a deformable reservoirs.

4. A drug delivery system according to claim 3 wherein the deformable reservoir is a length of elastomeric tubing.

5. A drug delivery system according to claim 3 wherein the deformable reservoir is an elastomeric balloon member.

6. A drug delivery system according to claim 3 further comprising a housing which at least partially surrounds the deformable reservoir and acts as a limiting means for restricting the deformation of the deformable reservoir.

7. A drug delivery system according to claim 6 wherein the housing is transparent and is capable of being dismantled to allow the deformable reservoir to be serviced or replaced as required.

8. A drug delivery system according to claim 1 further comprising a means for the continuous delivery of a drug to a patient.

9. A drug delivery system according to claim 8 wherein the means for continuous delivery of a drug to a patient is provided via a conduit which is in fluid communication between the main reservoir and the patient line.

10. A drug delivery system according to claim 9 wherein the conduit is flow control. tubing.

11. A drug delivery system according to claim 9 wherein a second flow regulating means is located in-line in the conduit.

12. A drug delivery system according to claim 11 wherein the conduit between the flow regulating means and the patient line is flow control tubing.

13. A drug delivery system according to claim 8 wherein the means for continuous delivery of a drug to a patient is provided via a secondary drug delivery system comprising a secondary reservoir which is in fluid communication with the patient line via a conduit.

14. A drug delivery system according to claim 13 wherein secondary reservoir is pressure driven.

15. A drug delivery system according to claim 13 wherein the conduit is flow control tubing.

16. A drug delivery system according to claim 13 wherein a second flow regulating means is located in-line in the conduit between the secondary reservoir and the patient line.

17. A drug delivery system according to claim 16 wherein the conduit between the flow regulating means and the patient line is flow control tubing.

18. A drug delivery system according to claim 1 wherein the patient line incorporates an air filter.

19. A drug delivery system according to claim 1 wherein the patient-line comprises flow control tubing.

* * * * *